(12) United States Patent
Coenen et al.

(10) Patent No.: US 11,607,168 B2
(45) Date of Patent: Mar. 21, 2023

(54) METHOD OF ASSESSING HAIR

(71) Applicant: Conopco, Inc., Englewood Cliffs, NJ (US)

(72) Inventors: Gita Coenen, Liverpool (GB);
Deborah Kirsten Lunt, Wirral (GB);
Stephen Paul Maguire, Liverpool (GB); Scott Robson, Bromborough (GB); Shona Elizabeth Simmons, Chester (GB); Geraldine Bridget Griffith, Chester (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 880 days.

(21) Appl. No.: 16/464,577

(22) PCT Filed: Nov. 13, 2017

(86) PCT No.: PCT/EP2017/079022
§ 371 (c)(1),
(2) Date: May 28, 2019

(87) PCT Pub. No.: WO2018/099715
PCT Pub. Date: Jun. 7, 2018

(65) Prior Publication Data
US 2021/0100494 A1 Apr. 8, 2021

(30) Foreign Application Priority Data

Nov. 30, 2016 (EP) ..................... 16201536

(51) Int. Cl.
*A61B 5/00* (2006.01)
*G01N 1/30* (2006.01)
(Continued)

(52) U.S. Cl.
CPC ............... *A61B 5/448* (2013.01); *G01N 1/30* (2013.01); *G01N 3/08* (2013.01); *G01N 33/4833* (2013.01)

(58) Field of Classification Search
CPC . A61B 5/448; G01N 1/30; G01N 3/08; G01N 33/4833
See application file for complete search history.

(56) References Cited

U.S. PATENT DOCUMENTS 1,458,529 A 12/1923 Hill
3,081,780 A * 3/1963 Cramer ............... A41G 3/0075
132/201

(Continued)

FOREIGN PATENT DOCUMENTS

CN 1391098 1/2003
CN 1886646 12/2006
(Continued)

OTHER PUBLICATIONS

Substantiating Claims for Hair Care Products personal care: M. Brandt et al. (Year: 2016).*
(Continued)

*Primary Examiner* — John Fitzgerald
*Assistant Examiner* — Gedeon M Kidanu
(74) *Attorney, Agent, or Firm* — Krista A. Kostiew

(57) ABSTRACT

A method for assessing the state of hair by releasably engaging a first end (5) of hair fibres (3) with a holder (1) so that an opposite, second end (4) of said hair fibres (3) hangs free and applying sufficient force to the first end (5) of the hair fibres (3) such that the hair fibres (3) at the second end (4) are pulled across the holder (1), wherein the force is in an upwards direction and applied by action of an encapsulated gas having a density of less than that of air (7).

17 Claims, 2 Drawing Sheets

Figure 1:
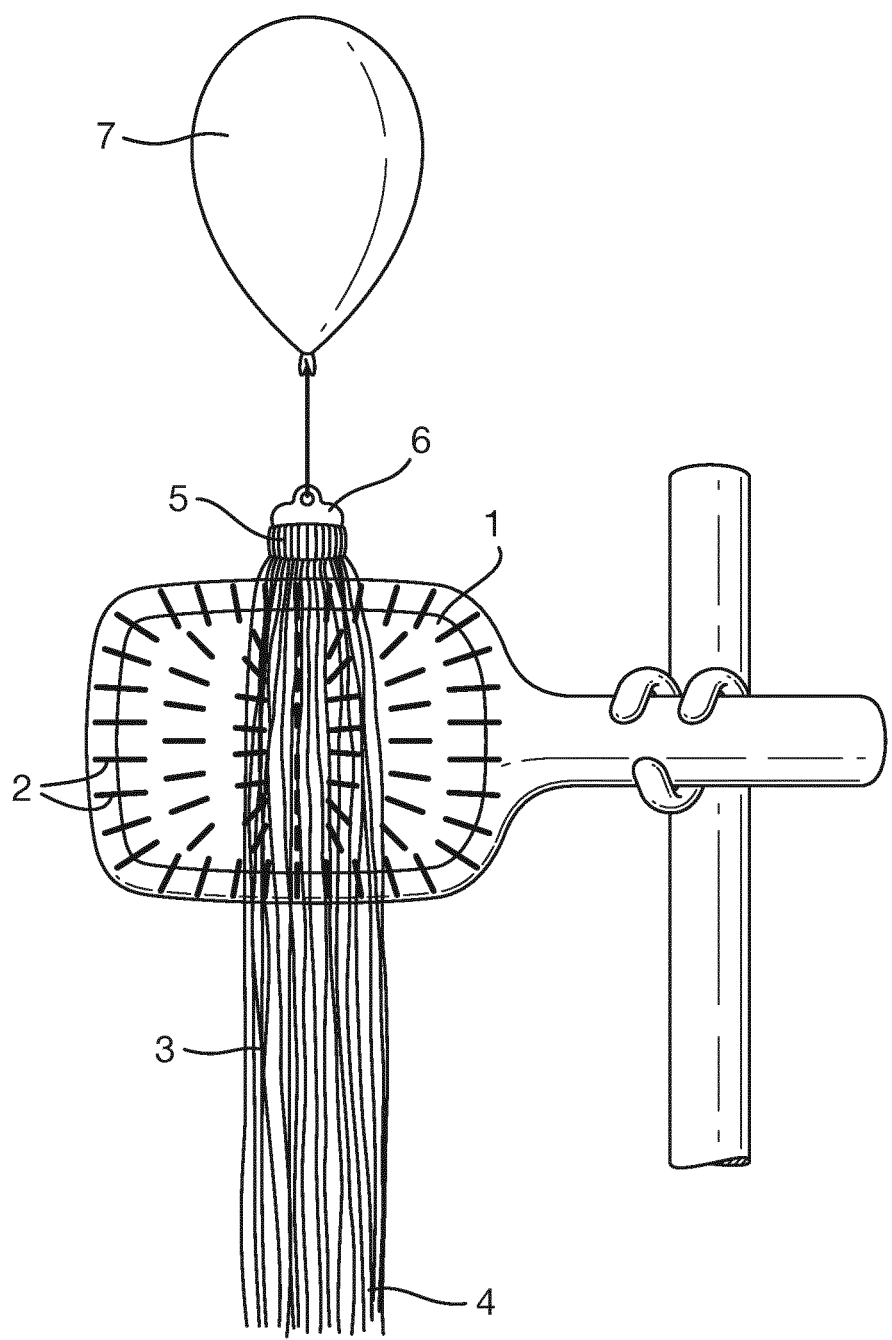

(51) Int. Cl.
  *G01N 3/08* (2006.01)
  *G01N 33/483* (2006.01)

(56) References Cited

U.S. PATENT DOCUMENTS

| | | | |
|---|---|---|---|
| 3,921,443 | A | 11/1975 | Yates |
| 3,946,606 | A | 3/1976 | Abrioux et al. |
| 4,061,022 | A | 6/1977 | Yates |
| 4,167,869 | A | 9/1979 | Gikas |
| 4,628,742 | A | 12/1986 | Golding |
| 4,628,747 | A | 12/1986 | Weitz et al. |
| 4,665,741 | A | 5/1987 | Kabacoff et al. |
| 6,817,222 | B2 | 11/2004 | Day et al. |
| 7,472,577 | B2 | 6/2009 | Shibuichi et al. |
| RE41,046 | E | 12/2009 | Cohen |
| 7,928,739 | B2 | 4/2011 | Sherman |
| 8,151,624 | B2 | 10/2012 | Sherman et al. |
| 8,429,963 | B2 | 4/2013 | Yagnik et al. |
| 8,833,137 | B2 | 9/2014 | Yagnik et al. |
| 8,998,002 | B1 * | 4/2015 | Milner ............... A47F 7/00 211/13.1 |
| 2003/0233861 | A1 | 12/2003 | Woolston et al. |
| 2006/0184068 | A1 | 8/2006 | Shibuichi et al. |
| 2007/0028680 | A1 | 2/2007 | Brouwers et al. |
| 2008/0025936 | A1 | 1/2008 | Keller et al. |
| 2009/0071228 | A1 | 3/2009 | Sherman et al. |
| 2012/0222466 | A1 | 9/2012 | Bailey et al. |
| 2013/0213127 | A1 | 8/2013 | Tynan, Jr. et al. |
| 2015/0260635 | A1 | 9/2015 | White |
| 2015/0355063 | A1 | 12/2015 | Fawcett et al. |
| 2016/0061809 | A1 | 3/2016 | Meinert et al. |
| 2018/0066394 | A1 * | 3/2018 | Salazar ............ A45D 44/02 |

FOREIGN PATENT DOCUMENTS

| | | | |
|---|---|---|---|
| CN | 101620052 | | 1/2010 |
| CN | 201607372 | | 10/2010 |
| CN | 102216754 | | 10/2011 |
| CN | 102713558 | | 10/2012 |
| CN | 202837269 U | * | 3/2013 |
| CN | 104956203 | | 9/2015 |
| DE | 19924741 | | 12/2000 |
| EP | 3015099 | | 5/2016 |
| JP | 56027652 A | | 3/1981 |
| JP | 56094260 A | | 7/1981 |
| JP | 63163143 | | 7/1988 |
| JP | 3152439 | | 6/1991 |
| JP | 4098146 | | 3/1992 |
| JP | 2517848 Y2 | * | 11/1996 |
| JP | H09131689 | | 5/1997 |
| JP | H09131689 A | * | 9/1997 |
| JP | 2004326971 | | 11/2004 |
| WO | WO07108318 | | 9/2007 |
| WO | WO2011068718 | | 6/2011 |
| WO | WO-2011068718 A1 | * | 6/2011 .......... A61B 5/1072 |
| WO | WO-2012173963 A1 | * | 12/2012 ............ B29C 53/32 |
| WO | WO2012173963 A1 | | 12/2012 |
| WO | WO2014117907 | | 8/2014 |
| WO | WO-2014117907 A1 | * | 8/2014 .............. G01N 1/28 |

OTHER PUBLICATIONS

IPRP1 in PCTEP2017079022; Jun. 4, 2019; World Intellectual Property Org. (WIPO).

Zhenming Hu et al.; Discussions of Estimation Methods of Shampoo Performances; Daily Chemical Industry; Oct. 31, 2002; pp. 65-68 (no English translation available); vol. 32 No. 5; China Surfactant Detergent & Cosmetics; China.

IPRP1 in PCTEP2013077662; Aug. 5, 2015; World Intellectual Property Org. (WIPO).

Co-pending Application, Fawcett et al., Jul. 20, 2015, U.S. Appl. No. 14/762,111.

Garcia et al.; Combability Measurements on Human Hair; Journal of the Society of Cosmetic Chemists; Sep. 1, 1976; pp. 379-398; XP008184761; vol. 27.

Brandt et al.; Substantiating Claims for Hair Care Products; sofw Journal Home and Personal Care Ingredients and Formulations; Jun. 8, 2016; pp. 1-8; XP055376763.

Trefor Evans, PHD; Evaluating Hair Conditioning with Instrumental Combing; Cosmetics and Toiletries; Aug. 1, 2011; pp. 558-563; XP8184763 ; vol. 126—No. 8.

Search Report and Written Opinion in PCTEP2017079022; dated Feb. 2, 2018.

Weitai Chen; Study on the Testing Method of Easy-combing Properties of the Wig; China Master's Theses Full-text Database Engineering Technology ; 2011; pp. B018-B034 (no English translation available); vol. 1.

Juntao Xia et al.; Hair care effect of a polymeric conditioning agent and characterization thereof; International Surfactant-Detergent Meeting ; 2006; pp. 220-226 (no English translation available); 9th.

Search Report and Written Opinion in EP16201536; dated Jun. 7, 2017.

Newman, et al., ; A Quantitative Characterization of Combing Force; J. Soc. Cosmet. Chem.; Dec. 9, 1973; pp. 773-782; 24.

Vaynberg et al.; The Aqualong SLT: A novel device for measuring hair stiffness and lubricity; Journal of Cosmetic Science; Apr. 1, 2009; pp. 135-141; 60; United States of America.

Ishii; Objective and Instrumental Methods for Evaluation of Hair Care Product Efficacy and Substantiation of Claims; Hair and Hair Care; 1997; 267-269, 296-297; Chap 10; United States of America.

Search Report in PCTEP2013077662; dated Apr. 2, 2014.

Written Opinion in PCTEP2013077662; dated Apr. 2, 2014.

Written Opinion in EP13153649; dated Jul. 30, 2013.

Search Report in EP13153649; dated Jul. 30, 2013.

* cited by examiner

METHOD OF ASSESSING HAIR

CROSS REFERENCE TO RELATED APPLICATIONS

The present application is a U.S. National Phase Application under 35 U.S.C. § 371 of International Application No. PCT/EP2017/079022 filed on Nov. 13, 2017, which claims priority to European patent application No. 16201536.6 filed on Nov. 30, 2016, the contents of which are incorporated herein in their entireties.

The present invention relates to a method for assessing the state of hair fibres, the efficacy of conditioning compositions on said fibres and methods for assessing and comparing the efficacy of conditioning compositions.

WO2012/173963A1 discloses using mechanized strategies to fabricate test samples as well as strategies for selecting sample substrates.

JP S56 94260 (Sharp KK) discloses a method for assessing the state of hair where the breaking point is measured.

JP S56 27652 (Sharp KK) discloses a similar method where the hair is clamped on a capillary tube.

WO2014/117907 discloses a method for assessing the state of hair by releasably engaging a first end of hair fibres with a holder so that an opposite, second end of said hair fibres hangs free and applying sufficient force to the second end of the hair fibres such that the hair fibres at the first end are pulled from the holder. Weights are hung to the free end of wet hair switches that have been treated with conditioner compositions, to enable differences between the effect of different treatments to be determined.

Despite the prior art there remains a need for improved methods for demonstrating the condition of hair fibres.

We have found that for dry hair, less force is required than for wet hair. The use of a force in an upwards direction more closely mimics the action of a hair brush or combing means through the hair by a user, as the hair remains in a substantially "upright" configuration. We have found that this can be achieved by a method of applying force based on the principle of the rising of gases that have a density of less than that of air (the so-called "lifting" or "lift" gases), as opposed to gravity. It is particularly effective on dry hair.

Accordingly, and in a first aspect, there is provided a method for assessing the state of hair by releasably engaging a first end of hair fibres with a holder so that an opposite, second end of said hair fibres hangs free and applying sufficient force to the first end of the hair fibres such that the hair fibres at the second end are pulled across the holder, wherein the force is in an upwards direction and applied by action of an encapsulated gas having a density of less than that of air.

Preferably, the holder comprises bristles or tines. More preferably, the holder is selected from a hair brush and a comb and most preferably is a hair brush. Where the holder comprises bristles or tines, it is preferred that the hair fibres are pulled through the bristles or tines as force is applied to the first end. More preferably, the holder comprises bristles or tines which extend in a direction away from the direction of applied force. Preferably, the bristles or tines extend in a direction perpendicular to the fibres.

Preferably, the force is applied in a direction away from the holder.

Preferably, the method comprises recording the force applied for the hair switch. Preferably, the method further comprises comparing the force applied to one hair switch with the force applied to another hair switch required to achieve the same or comparable result. The friction arising when the hair fibres are pulled across the holder may be recorded.

Preferably, the force is sufficient to pull the hair completely from the holder. Preferably, the force is the minimum force required to pull all the fibres from the holder within a period of from 5 seconds to two minutes, preferably from 10 seconds to one minute from first application of force.

Preferably, the encapsulated gas is encapsulated in a balloon or balloons. Suitable gases are those that have densities lower than that of air (the so-called "lifting" or "lift" gases), for example, water vapour, hot air, methane, helium and hydrogen. Preferably, the gas is selected from helium and hydrogen, and most preferably is helium.

The method provides an easily demonstrable approach to assessing the state of the hair, more preferably, the state of tanglement of the hair fibres and/or the level of friction on the surface of the hair.

Preferably, a clip is attached to the first end of hair fibres and gas is added in progressively larger amounts to the clip, for example by further inflating a balloon or by adding more balloons.

Preferably, the hair fibres are in the form of hair switches and preferably are from 1 to 5 g switches, more preferably 1.5 to 3 g switches. Preferably the switches are bound at the first end, for example by means of gluing or tying.

Preferably the switches are from 10 to 50 cm in length, more preferably from 15 to 30 cm in length and most preferably from 20 to 28 cm in length.

Should the hair be significantly tangled then the force required to pull the hair fibres from the holder is greater than for not significantly tangled hair. Further, where there is a comparison between two or more hair switches of differing degrees of tanglement one will pull through the hair more easily, or with less force than the other. This would thus provide a purposeful demonstration of the efficacy of one conditioning treatment over another. Similarly, for two or more hair switches of differing degrees of surface roughness one will pull through the hair more easily, or with less force than the other. This is due to increased friction between fibres.

Preferably the hair is dry. The hair can be heat dried or air dried, preferably air dried, most preferably blow dried or dried naturally.

Preferably, the hair is treated with a conditioning composition and preferably dried before the hair is attached to the holder. This allows the operator to assess the efficacy of the conditioning composition by measuring the force required to pull the hair fibres from the holder.

Preferably the applied conditioning composition is a rinse-off conditioning composition.

In addition, it is apparently clear to those skilled in the art that there is no obstacle to use the present invention for assessing the state of wet hair. Those skilled in the art would be able to measure the force required to pull the wet hair from the holder. The force shall also be in the upward direction. Generally, greater force and/or longer time to pull might be required than assessing dry hair. But it is still within the scope of invention.

In a second aspect there is provided a method for measuring the conditioning efficacy of a conditioning composition by applying a conditioning composition to hair, optionally rinsing, and then drying the hair, and releasably engaging the hair with the holder and then measuring the force required to pull the hair from the holder. The conditioning composition may be selected from a rinse-off or a leave-in conditioner.

Preferably, the time taken to pull the hair from the holder is sufficiently short for an easy record to be made but not so short that the hair is pulled immediately from the holder.

In a third aspect there is provided a method for comparing the conditioning efficacy of at least two conditioning compositions by performing the method of the second aspect on the treated hair samples.

Preferably, the method of comparing the conditioning efficacy of at least two conditioning compositions is conducted simultaneously on the treated hair samples.

This allows the operator to immediately determine superiority of one composition over another without the need to measure the force involved or the time taken to pull the hair through the holder.

Preferably, the first encapsulated gas attached to the hair fibres provides insufficient force to pull the hair fibres from the holder and additional gas is sequentially added in a manner which permits differentiation between the two sets of hair fibres. In other words, identical force is applied to each set of hair fibres simultaneously until one of the sets of hair fibres is pulled from the holder and the other is maintained attached to the holder. This will demonstrate superiority of the conditioning efficacy of the composition treating the former set of hair fibres over that applied to the latter.

The method as described may also comprise a step of capturing one or more images of the upwards forces (e.g. the balloons) and hair. The images may be stored and/or transmitted for display on one or more visible display units. The display unit is preferably a screen.

FIG. 1 shows a brush (1) with extending bristles (2). A hair switch (3) is placed onto the brush (1) such that the lower (second) end (4) hangs loose. At the first (top) end (5) of each of the switches is a clip (6) with an encapsulated gas balloon (7) tied thereto.

Figure 2:
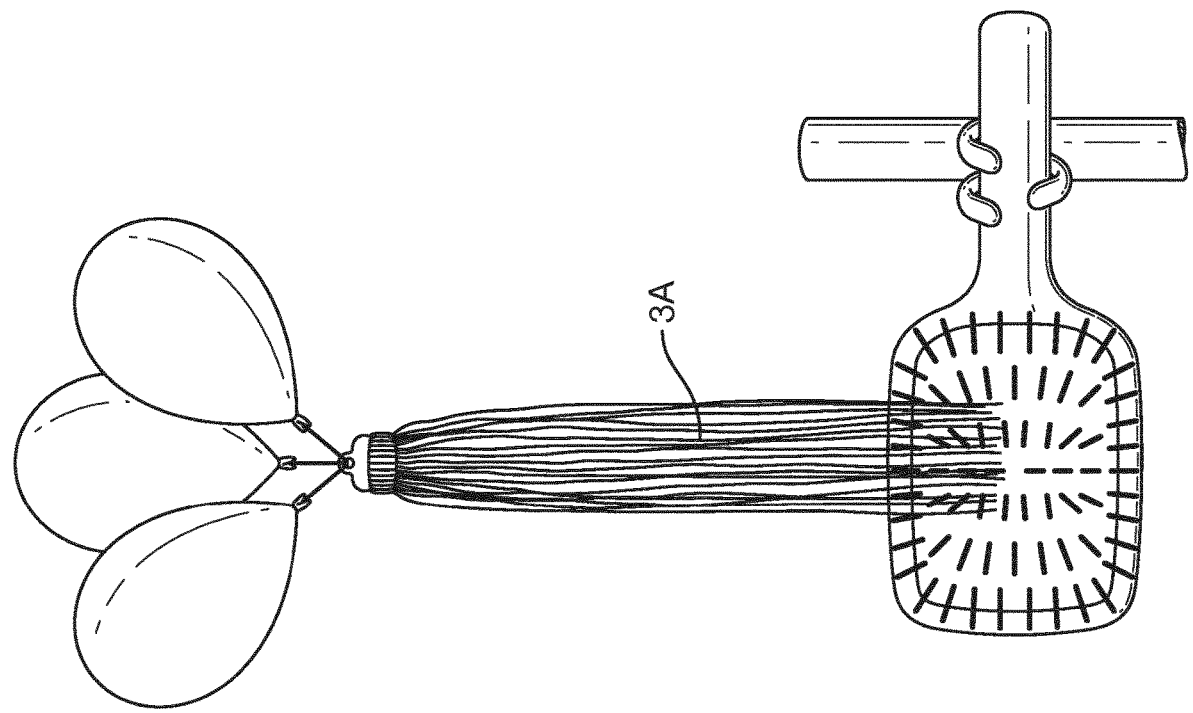
Figure 2:
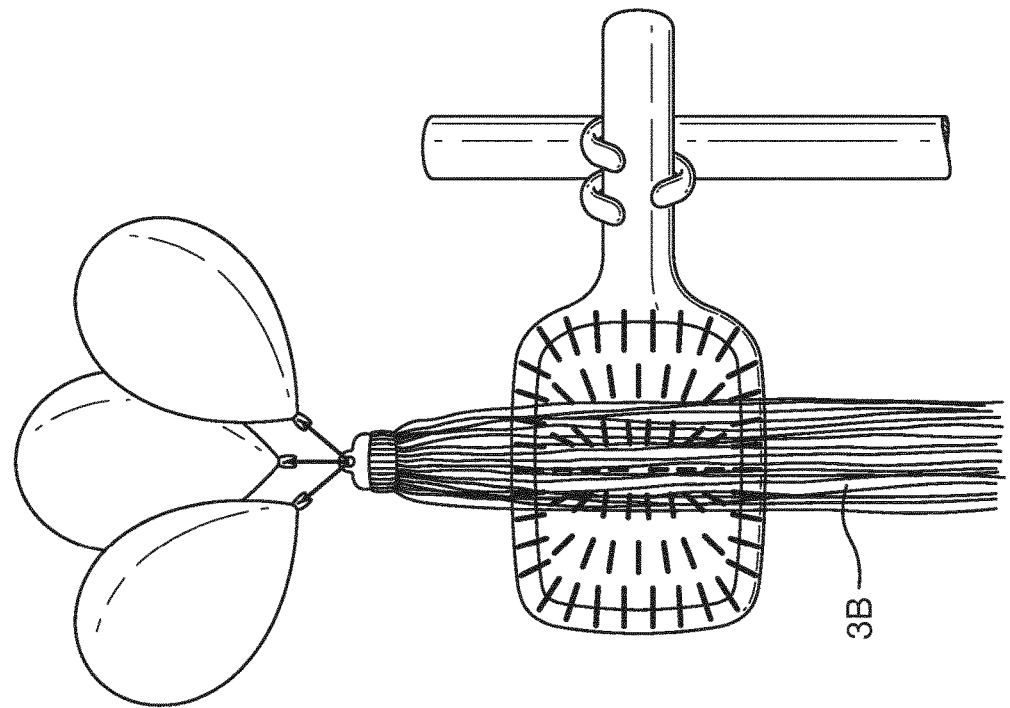

FIG. 2 shows a pair of switches, each as described in FIG. 1. Switch 3A is pulled more easily from the brush than switch 3B.

EXAMPLE 1

A hair switch was treated with Tresemme Expert Selection Beauty-Full Volume Pre wash conditioner and shampoo, rinsed and dried with a hair dryer.

A brush was held in position with a clamp and a switch of hair was positioned across the brush such that the top (first) end was at the top edge of the brush and the second (bottom) end was left to hang freely. A clip was attached to the top end of the hair fibres and an encapsulated gas balloon attached to the clip. Further balloons were added to the clip until the hair switch was pulled upwards through the brush. The switch was pulled right through the brush and floated upwards with the balloons.

EXAMPLE 2

The experiment of example 1 was repeated but with two hair switches treated with different conditioning compositions.

The conditioning treatments were Tresemme Expert Selection Beauty-Full Volume pre-wash conditioner and shampoo and Pantene Pro-V Volume and Body shampoo and conditioner, all commercially available.

The two switches are treated, rinsed for 10 seconds and dried as above.

Equal amounts of encapsulated gas (helium gas in standard rubber balloons) were attached to the clips of each switch simultaneously until sufficient gas was added such that the switch was pulled upwards through the brush.

The switch which was pulled from the brush most easily was considered to be the best conditioned.

It was found that the switch treated with the Tresemme product passed completely through the brush when 4 balloons were attached. The corresponding switch treated with the Pantene product only moved about half its length through the brush, with the same number of balloons.

The invention claimed is:

1. A method for assessing a state of hair by:
releasably engaging a first end (5) of hair fibres (3) with a holder (1) so that an opposite, second end (4) of said hair fibres (3) hangs free; and
applying sufficient force to the first end (5) of the hair fibres (3) such that the hair fibres at the second end (4) are pulled across the holder (1),
wherein the force is in an upwards direction and applied by action of an encapsulated gas having a density of less than that of air (7);
further comprising recording the force applied to the hair fibres (3); and
comparing the force applied to the hair fibres (3) with the force applied to other hair fibres required to achieve the same or comparable result to assess the state of the hair.

2. The method according to claim 1, wherein the hair (3) is dry.

3. The method according to claim 1, wherein the holder comprises bristles or tines.

4. The method according to claim 1, wherein the force is applied in a direction away from the holder.

5. The method according to claim 1, wherein the encapsulated gas is selected from a group consisting of water vapour, hot air, methane, helium, and hydrogen.

6. The method according to claim 1, wherein the encapsulated gas is encapsulated in a balloon or balloons.

7. The method according to claim 1, wherein the hair fibres (3) are in the form of hair switches.

8. The method according to claim 1, wherein the force is the minimum force required to pull all the fibres (3) from the holder (1) within a period from 5 seconds to two minutes from the first application of force.

9. The method according to claim 8, wherein the period is from 10 seconds to 1 minute from the first application of force.

10. The method according to claim 1, wherein the method further comprises:
capturing one or more images of the force (7) and hair (3); and
storing and/or transmitting the images.

11. The method according to claim 10, wherein the image(s) is displayed on one or more visible display units.

12. The method according to claim 11, wherein the display unit is a screen.

13. The method according to claim 1, wherein the hair (3) is treated with a conditioning composition prior to engaging the first end (5) of hair fibres (3) to the holder (1).

14. The method according to claim 13, wherein the composition is a rinse-off conditioning composition.

15. A method for measuring or demonstrating the conditioning efficacy of a conditioning composition by:
performing the method of claim 13; and
then measuring the force (7) required to pull the first end (5) from the holder (1).

16. A method for comparing or demonstrating the conditioning efficacy of at least two conditioning compositions by performing the method of claim 13 on each set of the treated hair samples (3).

17. The method according to claim 16, wherein the method of claim 3 is conducted simultaneously on each of the treated hair samples (3).

\* \* \* \* \*